United States Patent [19]

Nair

[11] Patent Number: 4,992,427
[45] Date of Patent: Feb. 12, 1991

[54] 2-SUBSTITUTED INOSINES AND THEIR USE AS ANTIVIRAL AGENTS

[75] Inventor: Vasu Nair, Iowa City, Iowa

[73] Assignee: University of Iowa Research Foundation, Iowa City, Iowa

[21] Appl. No.: 366,425

[22] Filed: Jun. 15, 1989

Related U.S. Application Data

[63] Continuation-in-part of Ser. No. 67,498, Jun. 29, 1987, abandoned.

[51] Int. Cl.$^5$ .................... A61K 31/70; C07H 19/167
[52] U.S. Cl. ........................................ 514/45; 514/46; 536/24; 536/26
[58] Field of Search ...................... 514/45, 46; 536/24, 536/26

[56] References Cited

FOREIGN PATENT DOCUMENTS 0038157 1/1969 Japan.

OTHER PUBLICATIONS

Nair et al., J. Am. Chem. Soc., 109, 7223–7224 (1987).

*Primary Examiner*—John W. Rollins
*Assistant Examiner*—L. Eric Crane
*Attorney, Agent, or Firm*—Zarley McKee, Thomte, Voorhees & Sease

[57] ABSTRACT

Certain functionalized inosines, preferably $C_2$ alkylated inosines, are prepared as new compounds having use as antiviral agents against viruses.

6 Claims, No Drawings

2-SUBSTITUTED INOSINES AND THEIR USE AS ANTIVIRAL AGENTS

CROSS-REFERENCE TO A RELATED APPLICATION

This application is a continuation-in-part of Ser. No. 067,498 filed June 29, 1987, now abandoned.

BACKGROUND OF THE INVENTION

A number of viral induced diseases pose serious world-wide health problems for which effective chemotherapeutic agents must be developed. Although many chemotherapeutic agents are available clinically for the treatment of diseases caused by microorganisms (e.g. bacteria), the same cannot be said for viral diseases. At present, only a few effective antiviral nucleosides are known but most of these compounds are useful against only DNA viruses as opposed to RNA viruses.

The search for purine nucleosides with antiviral activity against RNA viruses requires a understanding of the many complex biological pathways involving purine metabolism in mammalian systems as well as some understanding of viral metabolism. It has now been found that strategically functionalized compounds related to natural inosine may be metabolically stable with respect to key mammalian enzymes of purine metabolism but may be phosphorylated by less specific RNA viral enzymes in viral infected cells and thus may inhibit viral replication.

The primary object of the present invention is to provide alkylated inosines, preferably C-2 alkylated inosines which have antiviral activity against certain RNA arboviruses.

Another object of the present invention is to provide a method for use of alkylated inosine derivatives as antiviral agents.

A yet further object of the present invention is to provide an effective and direct route of synthesis of alkylated inosines which allows those to be economically and conveniently available for use in therapeutic treatments against RNA viruses.

A still further objective is to provide therapeutic compositions useful as antivirals for RNA viruses.

SUMMARY OF THE INVENTION

The present invention is concerned with three new compounds, 2-acetonylinosine, 2-vinylinosine, and its prodrug form [6-methoxy-2-vinyl-9-($\beta$-D-ribofuranosyl)purine], which have been discovered to have antiviral effect, particularly against RNA viruses. The invention also relates to a method of preparation of this class of inosines, the method of use of these functionalized inosines for therapeutic activity against RNA viruses and to compositions which accomplish the same.

DETAILED DESCRIPTION OF THE INVENTION

The inosine compounds described represent a new class of nucleosides with antiviral activity against RNA viruses. Those RNA viruses against which there is demonstrated antiviral activity may include the following families: Bunya, Alpha, Arena, Flavil, Rhabdo and Adeno. Cell lines used include Vero and Hep-2.

The alkylated inosine derivatives of the present invention are concerned with three compounds of the following structures:

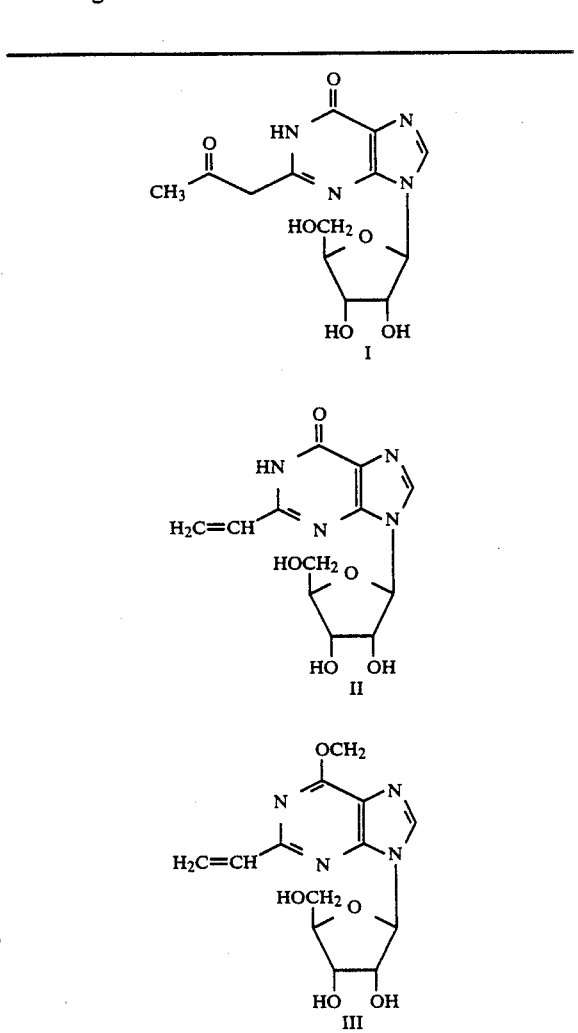

| (I)   | 2-Acetonyl-9-($\beta$-D-ribofuranosyl)-hypoxanthine or 2-Acetonylinosine |
| (II)  | 2-Vinyl-9-($\beta$-D-ribofuranosyl)-hypoxanthine or 2-Vinylinosine |
| (III) | 6-Methoxy derivative of II, i.e., 6-Methoxy-2-vinyl-9-($\beta$-D-ribofuranosyl)purine |

While the above compounds (I-III) represent the most strongly preferred 2-functionalized inosines, the 2-substituent may, in fact, be other groups such as —CH$_2$CH$_2$OH,

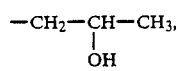

—CHO, —CH$_2$OH, and —CN.

The compounds of the present invention may be represented by the following general formula:

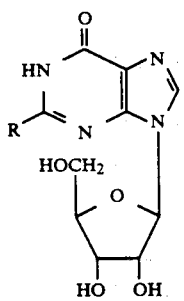

wherein R is selected from the group consisting of acetonyl and vinyl, and the 6-alkoxy (preferably 6-methoxy) derivative of the compound where R is 2-vinyl.

The preferred compounds of this invention (I, II, III) can be prepared in an efficient and fairly straightforward synthesis, which is schematically represented here.

reactions include radical deamination-halogenation and functionalized carbon-carbon bond formation involving palladium catalysis.

A common precursor to these compounds is the 6-chloro-2-amino purine (COMPOUND IV) which can be prepared from natural guanosine in three steps a described in my previous paper, *Synthesis,* 1982, 670, which is incorporated herein by reference. Replacement of the chlorine group at the 6-position in COMPOUND IV with methoxide is accompanied by the desired deprotection of the acetate groups. Subsequent protection of the carbohydrate hydroxyl groups with t-butyldimethylsilyl chloride and imidazole in dimethylformamide gave COMPOUND V. The key step in the synthesis of COMPOUND I was the conversion of COMPOUND V to COMPOUND VI in very good yields by the palladium-catalyzed cross-coupling reaction of COMPOUND V with the tin enolate of acetone. This and related reactions discussed here are the first examples of the use of tin reagents in palladium-catalyzed coupling involving nucleosides. Deprotection of COMPOUND VI with trimethylsilyliodide followed

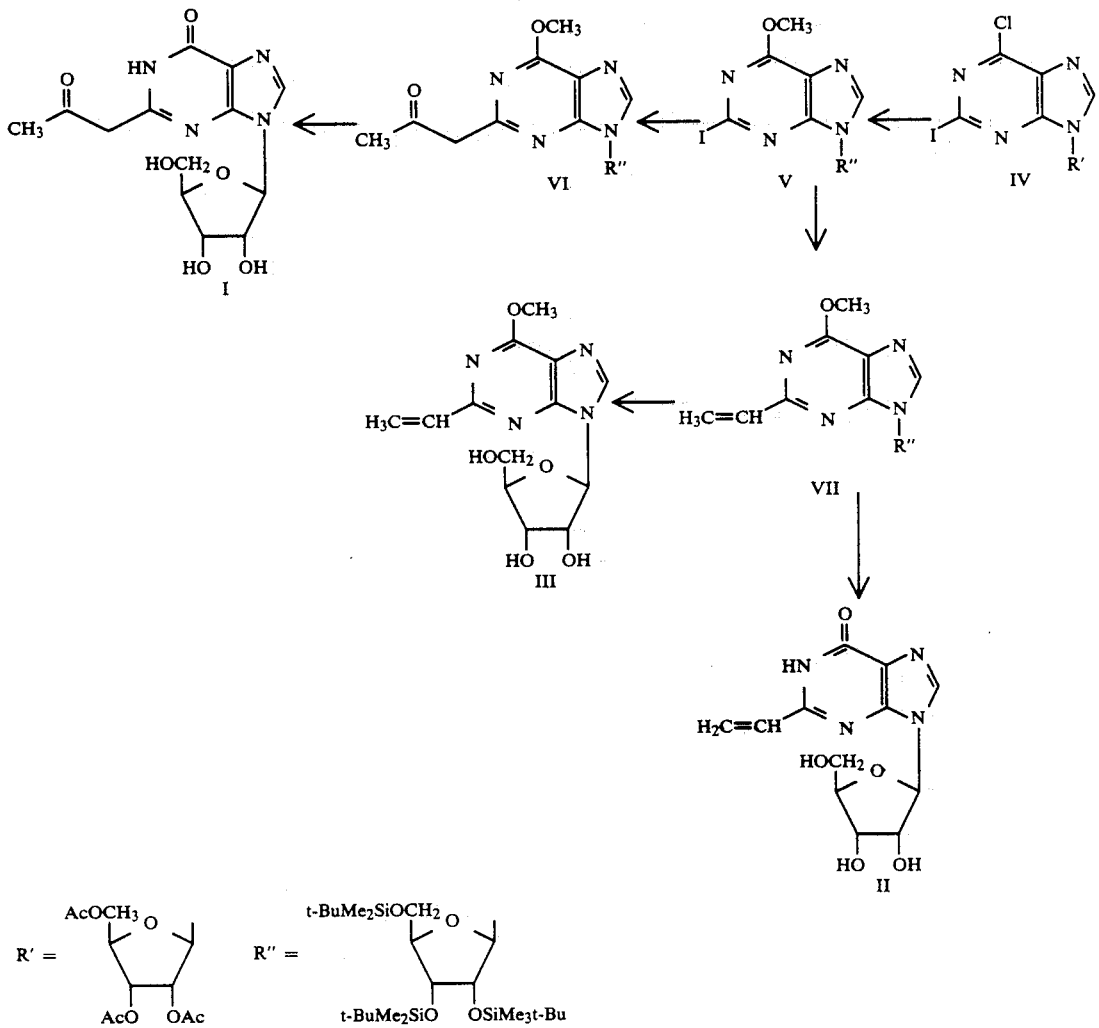

Generally speaking, the reactions for the formation of the functionalized 2-substituted purine nucleosides of this invention involve new applications of a combination of known chemical reactions. In particular, the key by tetrabutylammonium fluoride gave the preferred COMPOUND I of this invention. COMPOUND I and all other compounds described were purified to a high degree by multiple reversed-phase HPLC on Amberlite XAD-4 resin with ethanol-water as the eluting solvent. The structure of COMPOUND I, and also of other alkylated inosine compounds described, was established by elemental analysis, and ultraviolet, infrared, and NMR spectroscopy.

2-Vinylinosine (COMPOUND II) can be prepared in excellent yields from COMPOUND V by palladium-catalYzed coupling with vinyl tri-n-butyltin followed by deprotection of the intermediate COMPOUND VII.

Synthesis of 6-methoxy-2-vinyl-9-($\beta$-D-ribofuranosyl)purine (COMPOUND III) was achieved by desilylation of COMPOUND VII.

Some of the methodology used in the synthesis of COMPOUND I is given in my published paper regarding this subject, "Synthetic Approaches to Rare-Substituted Purine Nucleosides," presented at the 7th International Round Table Conference, Konstanz (F.R.G.), Sept. 29 –Oct. 3, 1986, and my paper "Synthetic Approaches to Rare-2-Substituted Purine Nucleosides, published in *Nucleosides and Nucleotides*, Issue No. 1, 1987, which represents an expanded abstract of the International Round Table Conference and which is incorporated hereby by reference.

The compounds and especially the preferred compounds (I and II) mentioned above from preliminary testing have considerable potential as antiviral agents against RNA viruses. For example, COMPOUND I exhibits antiviral activity against RNA viruses of the Bunya type with therapeutic index (T.I.) of greater than 1000 where a T.I. of greater than 1 (one) represents definite antiviral activity. COMPOUND II shows broad-spectrum antiviral activity against a number of RNA viruses. Such broad-spectrum antiviral activity is relatively rare for antiviral agents. COMPOUND III is the prodrug form of COMPOUND II.

Another aspect of the invention provides pharmaceutical compositions comprising one of the therapeutically active antiviral agents of the present invention or a pharmaceutically acceptable salt thereof, together with a pharmaceutically acceptable carrier therefor. In a particular aspect, pharmaceutical compositions comprise a compound of the present invention in a effective unit dosage form.

As used herein, the term "effective unit dosage" or "effective unit dose" is denoted to mean a predetermined antiviral amount sufficient to be effective against the viral organisms in vivo. Pharmaceutically acceptable carriers are materials useful for the purpose of administering the medicament, and may be solid, liquid or gaseous materials, which are otherwise inert and medically acceptable and are compatible with the active ingredients.

These pharmaceutical compositions may be given parenterally, orally, used as a suppository or pessary, applied topically as an ointment, cream, aerosol, powder, or given as eye or nose drops, etc., depending on whether the preparation is used to treat internal or external viral infections.

For internal infections, the compositions are administered orally or parenterally at dose levels, calculated as the free base, of about 0.1 to 250 mg per kg, preferably 1.0 to 50 mg. per kg, of mammal body weight, and are used in man in a unit dosage form, administered a few times daily in the amount of 1 to 250 mg per unit dose.

For oral administration, fine powders or granules may contain diluting, dispersing and/or surface active agents, and may be presented in a draught, in water or in a syrup; in capsules or sacnets in the dry state or in a non-aqueous solution or suspension, wherein suspended agents may be included; in tablets, wherein binders and lubricants may be included; or in a suspension in water or a syrup. Where desirable or necessary, flavouring, preserving, suspending, thickening, or emulsifying agents may be included. Tablets and granules are preferred and these may be coated.

For parenteral administration or for administration as drops, the compounds may be presented in an aqueous solution in a concentration from about 0.1% to about 10%, more preferably from about 0.1% to about 7%, most preferably from about 0.2% on a weight/volume basis. This solution may contain antioxidants, buffers, etc.

Of the compounds covered by the present invention, COMPOUND I, 2-acetonyl-9-($\beta$-D-ribofuranosyl)-hypoxanthine, also referred to as 2-acetonylinosine, and COMPOUND II, 2-vinyl-9-($\beta$ D-ribofuranosyl)hypoxanthine, also referred to as 2-vinylinosine, are the most preferred because of their useful antiviral activity. COMPOUND III, 6-methoxy-2-vinyl-9-($\beta$ D-ribofuranosyl)purine is the masked form of COMPOUND II, and III is easily converted to II by hydrolysis. COMPOUND III is thus a prodrug form of COMPOUND II.

In a yet further aspect of the present invention, there is provided a method of treating viral infections in mammals which comprises administering an effective non-toxic antiviral amount, as herein before defined, of a substituted purine of this invention or a pharmaceutically acceptable salt thereof. Administration is preferably by topical application or by the oral or parenteral route.

The following examples will illustrate the invention. In the examples, nuclear magnetic resonance spectra using tetramethylsilane as an internal standard were recorded on JEOL Model FX90Q and Bruker Model WM360 pulse Fourier transform spectrometers. A Hewlett-Packard 5985 GC/MX system was used for the mass spectra. The ultraviolet spectra were recorded on a Varian Cary Model 219 spectrophotometer. Infrared spectra were recorded on an IBM Model 98 Fourier transform instrument. Lyophilizations were performed with a Virtis freezemobile 3 unit. Preparative layer chromatography plates were prepared by coating six 20 cm $\times$ 20 cm plates with a slurry made from 150 g of E. Merk PF$_{254}$ silica gel in 400 mL of water. The silica gel plates were allowed to dry slowly and were then activated for three hours at 135° C. Flash chromatography was carried out using glass columns packed with 230–400 mesh silica gel. High performance liquid chromatography was done using Altex columns packed with Amberlite XAD-4 resin (Rohm and Haas) which was ground and sieved to 40-60 $\mu$m. Samples were injected with a gas tight syringe through an Altex 4-way slide valve. Separations were carried out at 20–80 psi using an FMI RRPSY-SS $\frac{1}{4}$ inch piston pump. Fractions were monitored by a Pharmacia UV-2 ultraviolet monitor and products were collected by a Gilson FC-100 fraction collector. Elemental analysis were performed by Galbraith Laboratories, Inc., Knoxville, Tennessee, and the results were within $\pm 0.4\%$ of the theoretical values.

EXAMPLE I

2-Iodo-6-methoxy-9-(2,3,5-tri-0-t-butyldimethylsilyl-β D-ribofuranosyl)purine (V)

Dry 6-chloro-2-iodo triacetylated nebularine (IV), 1.780 g (3.30 mmol) was taken up in dry (Omnisolve) methanol (50 mL) to which sodium methoxide (1.045 g, 19.35 mmol) was subsequently added. The solution was fitted with a septum and stirred at 25° C. for 12 hours. The reaction was quenched by heating (50° C.) with 1 g of NH$_4$Cl. After filtration, the solution was concentrated with in vacuo. The residue was absorbed on 5 grams of 230-400 mesh silica gel and added to the top of a 40 m flash chromatography column. The eluant was concentrated to give 1.059 g (2.60 mmmol, 78.6%) of product which was silylated with t-butyldimethylsilyl chloride (1.56 g), 10.40 mmol) and imidazole (1.414 g, 20.8 mmol) in dimethylformamide (20 mL). The product V was isolated as a low melting gum (1.560 g, 80% yield) after flash chromatography on silica gel: $^1$H NMR (CDCL$_3$)δ−0.02–0.13 (m, 18H), 0.90 (m, 27H), 3.71 to 4.63 (m, 5H), 4.13 (s, 3H), 5.93 (d, 1H), 8.20 (s, 1H); UV (EtOH)λ$_{max}$=262 (ε7.8×10$^3$); mass spectrum, m/z (relative intensity) 751 (M$^+$, 1.2), 693 (M$^+$, t Bu, 100), 433 (26.8), 285 (5.7), 261 (27.7), 231 (19.0), 211 (18.0), 175 (4.1), 155 (7.0), 147 (47.5), 129 (21.9), 115 (19.4).

EXAMPLE 2

2-Acetonyl-6-methoxy-9-(2,3,5-tri-0-t-butyldimethylsilyl-β-D-ribofuranosyl)

purine (VI)

Silylated 2-iodo-6-methoxynebularine (V) (1.208 g. 1.611 mmol) was weighed into a 100 mL RBF already containing palladium acetate (0.036 g, 0.161 mmol) and tris(o-tolyl)phosphine (0.098 g, 0.322 mmol), and the flask was placed on the vacuum pump to remove residual oxygen and moisture. Toluene (25 mL), freshly distilled from sodium hydride, was added under nitrogen. In a separate flask, toluene (10 mL), isopropenyl acetate (0.280 mL, 2.42 mmol) and tributyltin methoxide (0.70 mL, 2.42 mmol) were combined. This solution was kept at 40° C. for 30 minutes. The nucleoside solution was then transferred by double tipped needle to the flask containing the tin reagent. After heating this solution for 6 hours at 95° C., no starting material remained (tlc, 2:1 hexane:ether). The solution was cooled to room temperature and partitioned between ether (70 mL) and a 5% aqueous disodium ethylenediamine tetracarboxylic acid (Na$_2$ EDTA). The ether layer was then extracted with water (30 mL). The aqueous phases were back extracted with ether (30 mL) and the combined ether layers were dried (Na$_2$SO$_4$) and concentrated. The crude product was purified by flash chromatography, using 2:1 hexane:ether as the eluting solvent, to give the protected acetonylated product VI (0.7952 g, 1.17 mmol, 73%) as a low melting solid: $^{13}$C NMR (CDCl$_3$)δ−5.3, −4.9, −4.7, −4.3, 17.9, 18.1, 18.6, 25.7, 25.8, 26.1, 29.8, 54.1, 54.3, 62.2, 71.3, 76.1, 84.9, 88.6, 120.4, 141.0, 152.3, 158.4, 160.7, 204.3; $^1$H NMR (CDCl$_3$)δ−0.02 −0.13 (m, 18), 0.92 (m, 27H), 2.23 (s, 3H), 3.78 −4.05 (m, 3H), 3.98 (s, 2H), 4.13 (s, 3H), 4.30 (t, 1H), 4.52 (t, 1H), 6.03 (d, 1 H), 8.27 (s, 1 H); UV (EtOH)λ$_{max}$ 250 nm (ε9.0×10$^3$), 290 nm (2.7×10$^3$).

EXAMPLE 3

2-Acetonyl-9-(β-D-ribofuranosyl)hypoxanthine (I)

The protected acetonylated product (VI), (0.850 g, 1.25 mmol), was taken up in acetonitrile (25 mL) which was freshly distilled from calcium hydride. Potassium iodide which had been dried on the vacuum pump at 50° C. was added, followed by trimethylsilyl chloride via a gas tight syringe. The solution was stirred for 8 hours at room temperature. The solution was filtered, and the precipitate was washed with ether. The filtrate and ether washings were concentrated and purified by flash chromatography using ether as the eluting solvent to give the demethylated product (0.5305 g, 0.7965 mmol, 64% yield). This compound was dissolved in dry tetrahydrofuran (50 mL) and treated with 3.186 mmol of tetrabutylammonium fluoride in tetrahydrofuran (1 M solution). The solution was stirred until no starting material remained (2 hours). An aqueous solution of a ten fold excess of ammonium chloride was added and the tetrahydrofuran was removed in vacuo. The remaining aqueous solution was heated at 50-60° C. for 45 minutes. The aqueous phase was then extracted with chloroform (2×25 mL) and then with ether (2×25 mL). The aqueous phase was then concentrated under reduced pressure and the residue was purified by reversed-phase HPLC on Amberlite XAD-4 resin (40–60 μm) using ethanol-water as the mobile phase. The combined fractions containing the product were lyophilized to give a white powder: $^{13}$C NMR (DMSO-d$_6$)δ30.0, 49.2, 61.5, 70.6, 74.0, 85.8, 87.1, 122.8, 138.7, 148.5, 152.7, 157.0, 202.9; $^1$H NMR (DMSO-d$_6$)δ 2.23 (s, 3H), 3.59 (m, 2H), 3.92 (br.s, 3H), 4.11 (m, 1 H), 4.47 (m, 1 H), 5.11 (t, 1 H), 5.23 (d, 1 H), 5.50 (d, 1 H), 5.84 (d, 1 H) 8.32 (s, 1 H); UV (H$_2$O)λ$_{max}$ 250 nm (ε1.2×10$^4$), 266 (λ6.8×10$^3$); FTIR (KBr) 3317, 2961, 2934, 1701, 1692, 1687, 1585, 1558 cm$^{-1}$.

EXAMPLE 4

2-Vinyl-9-(β-D-ribofuranosyl)hypoxanthine (II)

The palladium catalyzed coupling reaction of V to give VII was carried out as described for VI (Example 2) but with the following modifications: (i) bis(acetonitrile) palladium chloride replaced palladium acetate, (ii) vinyl tri-n-butyltin replaced the mixture of tributyltin methoxide and isopropenyl acetate, (iii) the reaction time was reduced to 3 hours. The yield of VII from this reaction was 89%. The two-step deprotection of XI and purification of the resulting product were executed as described for I (Example 3). COMPOUND II was obtained in pure form as a lyophilized powder (50% yield, from VII) after multiple HPLC separations: $^{13}$C NMR (Me$_2$SO-d$_6$)δ 61.3, 70.4, 73.6, 85.6, 87.2, 123.2, 125.2, 129.5, 139.3, 148.5, 151.7, 156.8; $^1$H NMR (Me$_2$So-d$_6$)δ 3.62 (m, H 3.96 (m, 1H) 4.17 (m, 1 H), 4.56 (m, 1 H), 5.05 (t, 1H), 5.25 (d, 1H), 5.50 (d, 1H), 5.83 (dd, 1H), 5.91 (d, 1H), 6.50 (m, 2H), 8.35 (s, 1H), 12.41 (s, 1H); UV (H$_2$O)α$_{max}$ 292 nm (ε6,486), 260 nm (ε 7,850), 207 nm (ε19,891); FTIR (KBr) 3300, 3080, 2900, 1686, 1640, 1554 cm$^{-1}$.

EXAMPLE 5

6-Methoxy-2-Vinyl-9-(β-D-ribofuranosyl)purine (III)

Removal of the silyl protecting groups only from VII by treatment with tetrabutylammonium fluoride in tetrahydrofuran gave III: $^1$H NMR (Me$_2$SO-d$_6$)δ 3.62 (m, 2H), 3.98 (m, 1H), 4.13 (s, 3H), 4.31 (m, 1H), 4.62 (m, 1H), 5.14 (t, 1H), 5.24 (d, 1H), 5.50 (d, 1H), 5.73 (dd, 1H), 5.99 (d, 1H), 6.55 (dd, 1H), 6.77 (dd, 1H), 8.59 (s, 1h); UV (H$_2$O) 265 nm, 221 nm.

EXAMPLE 6

Antiviral Evaluation

Antiviral screening was done with a series of RNA viruses including viruses of the following families: Bunya, Alpha, Arena, Flavi, Rhadbo, and Adeno (TABLE 1). Cell lines used included Vero and Hep-2. Antiviral results suggest that COMPOUND 1 shows high antiviral activity against viruses of the Bunya family (e.g. Sandfly Fever virus). The therapeutic index (T.I.) is >1000 for 2-acetonyl-inosine on a scale where a T.I. of greater than 1 represents a compound with definite antiviral activity.

Therapeutic index (T.I.) is defined as the minimum toxic concentration divided by the I.D$_{50}$, which is the concentration of the drug that causes a 50% reduction in virus replication. COMPOUND II shows broad-spectrum antiviral activity against a number of RNA viruses which is relatively rare for antiviral agents. COMPOUND III is the masked form of COMPOUND II.

TABLE I

ANTIVIRAL ACTIVITY OF ALKLATED INOSINES AGAINST RNA VIRUSES
Therapeutic Index (Vero Cells)

| Virus | Compound I | Compound II |
|---|---|---|
| AD2 | 0 | 2.5 (7.1)* |
| JBE | 0 | 3.2 |
| PIC | 0 | 1.3 |
| PT | 0.3 | 3.7 |
| RVF | 0 | 2.1 |
| SF | >1000 | — |
| VSV | 0 | 0 |
| VV | 0 | 7.7 |
| YF | 0 | 1.3 |
| VEE | — | 0.1 |

*Hep-2 cell line.

These compounds when formulated in dosage levels as earlier described, 1 mg to 250 mg per kg of body weight may demonstrate antiviral activity against RNA viruses.

What is claimed is:

1. 2-substituted inosine or a pharmaceutically acceptable salt thereof of the formula:

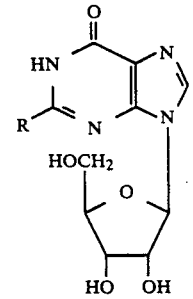

wherein R is selected from the group consisting of acetonyl and vinyl and the 6-methoxy derivative of the compound wherein R is 2-vinyl.

2. The compound of claim 1 wherein R is 2-acetonyl.
3. The compound of claim 1 wherein R is 2-vinyl.
4. The compound of claim 1 which is a 6-methoxy derivative of the compound wherein R is 2-vinyl.
5. A pharmaceutical composition which comprises a pharmaceutically acceptable carrier in combination with an effective non-toxic antiviral treating amount of a 2-substituted inosine or a pharmaceutically acceptable salt form thereof of the formula:

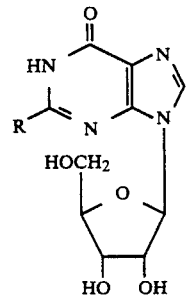

wherein R is selected from the group consisting of acetonyl and vinyl and the 6-methoxy derivative of the compound wherein R is 2-vinyl.

6. A method of treating RNA virus infections, said method comprising administering to an RNA virus infected mammal an effective non-toxic antiviral treating amount of a 2-substituted inosine or a pharmaceutically acceptable salt form thereof of the formula:

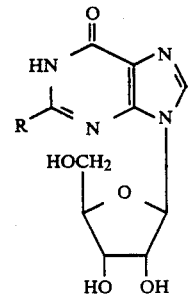

wherein R is selected from the group consisting of acetonyl and vinyl and the 6-methoxy derivative of the compound wherein R is 2-vinyl.

* * * * *

UNITED STATES PATENT AND TRADEMARK OFFICE
CERTIFICATE OF CORRECTION

PATENT NO. : 4,992,427
DATED : February 12, 1991
INVENTOR(S) : Vasu Nair

It is certified that error appears in the above-indentified patent and that said Letters Patent is hereby corrected as shown below:

Column 1, line 9 please add the following: Work for this invention was funded in part by a grant from the United States Army, grant number DAMD17-86-C-6001. The Government may have certain rights in this invention.

Signed and Sealed this

Fifteenth Day of November, 1994

Attest:

BRUCE LEHMAN

Attesting Officer    Commissioner of Patents and Trademarks